(12) United States Patent
Turner et al.

(10) Patent No.: US 7,769,468 B2
(45) Date of Patent: Aug. 3, 2010

(54) TRANSPARENT ELECTROMAGNETIC APPLICATOR AND HYPERTHERMIA TREATMENT METHOD

(75) Inventors: Paul F. Turner, Bountiful, UT (US); Mark Hagmann, Salt Lake City, UT (US); Thomas L. Youd, Salt Lake City, UT (US); Jason Lynn Elsworth, Salt Lake City, UT (US)

(73) Assignee: BSD Medical Corporation, Salt Lake City, UT (US)

( * ) Notice: Subject to any disclaimer, the term of this patent is extended or adjusted under 35 U.S.C. 154(b) by 1188 days.

(21) Appl. No.: 11/367,076

(22) Filed: Mar. 3, 2006

(65) Prior Publication Data
US 2007/0208399 A1    Sep. 6, 2007

(51) Int. Cl.
*A61B 18/18*    (2006.01)
*A61F 7/08*    (2006.01)
(52) U.S. Cl. .................... 607/100; 607/101; 607/102
(58) Field of Classification Search ......... 607/100–102, 607/154–156
See application file for complete search history.

(56) References Cited

U.S. PATENT DOCUMENTS

| | | | |
|---|---|---|---|
| 3,774,620 A | 11/1973 | Hansjurgens | |
| 4,095,602 A | 6/1978 | Leveen | |
| 4,140,130 A | 2/1979 | Storm, III | |
| 4,148,321 A | 4/1979 | Wyss et al. | |
| 4,190,053 A | 2/1980 | Sterzer | |
| 4,197,851 A * | 4/1980 | Fellus | 607/71 |
| 4,204,549 A | 5/1980 | Paglione | |
| 4,237,898 A | 12/1980 | Whalley | |
| 4,285,346 A | 8/1981 | Armitage | |
| 4,311,154 A | 1/1982 | Sterzer et al. | |
| 4,322,594 A | 3/1982 | Brisson | |
| 4,346,715 A | 8/1982 | Gammell | |
| 4,397,313 A | 8/1983 | Vaguine | |

(Continued)

FOREIGN PATENT DOCUMENTS

DE    4310070 A1 *    9/1994

(Continued)

OTHER PUBLICATIONS

Lee, Wilsey, Tarczy-Hornoch, Kapp, Fessenden, Lohrbach and Prionas, "Body Conformable 915 MHz Microstrip Array Applicators for Large Surface Area Hyperthermia"; IEEE Transactions on Biomedical Engineering, May 1992, pp. 470-483, vol. 39, No. 5.

(Continued)

*Primary Examiner*—Roy D Gibson
*Assistant Examiner*—Kaitlyn E Helling
(74) *Attorney, Agent, or Firm*—Thorpe North & Western LLP

(57) ABSTRACT

An applicator and method for application of electromagnetic energy to an area of tissue is described. The applicator includes a visually-transparent, high-dielectric interfacing assembly which has a conformable tissue-engaging surface and an opposed antenna-engaging surface. At least one balanced, circularly-polarized antenna is disposed in a plane substantially parallel and adjacent to the antenna-engaging surface. The interfacing assembly and at least one antenna are substantially transparent to enable visual viewing of the area of tissue. This enables monitoring of the tissue for adverse treatment effects while electromagnetic energy is being applied to the at least one antenna and radiated into the tissue.

34 Claims, 6 Drawing Sheets

U.S. PATENT DOCUMENTS

| | | | |
|---|---|---|---|
| 4,397,314 A | | 8/1983 | Vaguine |
| 4,411,266 A | | 10/1983 | Cosman |
| 4,412,540 A | * | 11/1983 | Bentall ................ 607/50 |
| 4,669,475 A | | 6/1987 | Turner |
| 4,672,980 A | | 6/1987 | Turner |
| 4,690,156 A | | 9/1987 | Kikuchi et al. |
| 4,712,559 A | | 12/1987 | Turner |
| 4,757,820 A | | 7/1988 | Itoh |
| 4,974,587 A | | 12/1990 | Turner et al. |
| 5,101,836 A | * | 4/1992 | Lee ..................... 607/155 |
| 5,364,336 A | * | 11/1994 | Carr ..................... 607/101 |
| 6,330,479 B1 | * | 12/2001 | Stauffer ................ 607/101 |
| 6,413,255 B1 | * | 7/2002 | Stern .................... 606/41 |

FOREIGN PATENT DOCUMENTS

| | | |
|---|---|---|
| EP | 0249532 A1 | 12/1987 |
| EP | 0251746 A1 | 1/1988 |
| GB | 2135891 A | 9/1984 |
| GB | 2151489 A | 7/1985 |

OTHER PUBLICATIONS

Samulski, Fessenden, Lee, Kapp, Tanabe and McEuen, "Spiral Microstrip Hyperthermia Applicators: Technical Design and Clinical Performance", Int. J. Radiation Oncology Biol. Phys., Jul. 1990, pp. 233-242, vol. 18, USA.

Ryan, Backus and Coughlin, "Large stationary microstrip arrays for superficial microwave hyperthermia at 433 MHz: SAR analysis and clinical data", Int. J. Hyperthermia, 1995, pp. 187-209, vol. 11, No. 2.

Kaiser, "The Archimedean Two-Wire Spiral Antenna", Ire Transactions on Antennas and Propagation, May 1960, pp. 312-323.

Fessenden, Kapp, Lee, Samulski, "Clinical Microwave Applicator Design", US.

* cited by examiner

TRANSPARENT ELECTROMAGNETIC APPLICATOR AND HYPERTHERMIA TREATMENT METHOD

BACKGROUND OF THE INVENTION

1. Field

This invention relates to electromagnetic therapy and more particularly to applicators for applying electromagnetic energy to a treatment site.

2. State of the Art

The use of electromagnetic (EM) energy in the heating arts has been utilized for many years. In recent years EM energy has been utilized in diathermy and hyperthermia to provide therapeutic heating to diseased tissue. The application of the frequencies used have typically ranged from 100 kHz to 2450 MHz.

The use of heating for cancer therapy is commonly called hyperthermia, which is one of the intended uses of embodiments of this invention. This may be in combination with other treatments such as surgery, ionizing radiation, and chemotherapy. In hyperthermia treatment it is common to attempt heating the diseased tissue to above about 40 degrees C., but undesirable complications can occur when the maximum tissue temperature exceeds about 45 to 46 degrees C. Some of these complications include damage to healthy normal tissue, ulceration, surface blisters, and burns.

Providing hyperthermia for superficial treatment (e.g., <3 cm) of surface tissues presents a number of unique challenges. Although various techniques for deep tissue heating have been developed, many of these approaches are unsuitable for use in surface hyperthermia. For example, one approach to deep tissue heating uses phased arrays of linearly polarized antennas. Linearly polarized antennas are used in such applications because of the predictability with which the fields superimpose. Variations in the dielectric constant of the tissue (for example, between bone, muscle, fat, and tumor) can, however, cause significant variations when the electric field is parallel to an interface between tissues, making it difficult to achieve even absorption of the EM energy into the target tissue area.

Another challenge for superficial treatment is that the treatment areas can be quite large. Conforming an applicator to the complex contours of the human body can be difficult. Uneven surfaces caused by scarring or diseased tissue further complicate this problem. Prior attempts to provide large area treatment coverage have included complex mechanical arrangements to allow mechanical scanning of antennas.

Accordingly, it has proven difficult to maintain even heating distributions using prior techniques. High heat regions can result in surface burning, while low heat regions can fail to provide a therapeutically adequate level of heat. Approximately 8 to 10 percent of patients receiving hyperthermia have received burns during treatment.

An additional difficulty with electromagnetic treatment is the desire to efficiently couple the energy into the tissue being treated while minimizing radiation of energy in other directions. For example, to prevent radiation of energy out the back side of treatment applicators, a ground plane is usually placed behind the antennas. While the ground plane is effective at helping to force radiation into the tissue, it is visually opaque. Accordingly, visual monitoring of the treatment site requires removal of the treatment applicator.

SUMMARY OF THE INVENTION

It has been recognized that there is a need for an improved applicator for application of electromagnetic energy to an area of tissue being treated.

One embodiment of the present invention includes an applicator for application of electromagnetic energy to an area of tissue. The applicator includes a visually-transparent interfacing assembly, having a conformable tissue-engaging surface and an opposed antenna-engaging surface. The interfacing assembly has a high dielectric constant, or is filled with a high dielectric constant material. The applicator also includes at least one balanced, circularly-polarized antenna disposed in a plane substantially parallel and adjacent to the antenna-engaging surface of the interfacing assembly. The antenna has sufficient open area to enable visual viewing of the tissue-engaging surface through the antenna and the interface assembly. A feed is coupled to the antenna to allow injection of electromagnetic energy into the antenna.

THE DRAWINGS

Other features of the invention will become more readily apparent from the following detailed description when read in conjunction with the drawings in which the accompanying drawings show the best modes currently contemplated for carrying out the invention, and wherein.

DETAILED DESCRIPTION OF THE ILLUSTRATED EMBODIMENTS

Figure 1:
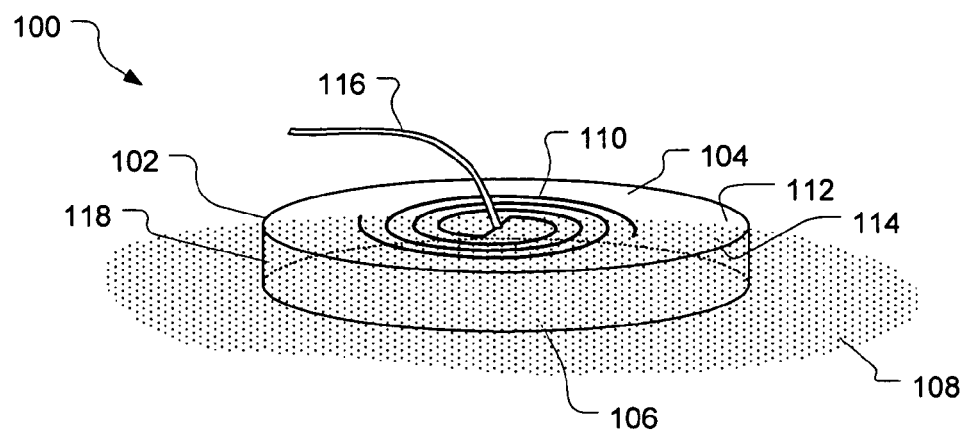
FIG. 1 is a perspective view of an applicator in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

An applicator for application of electromagnetic energy to an area of tissue is illustrated in FIG. 1 in accordance with an embodiment of the present invention. The applicator, shown generally at 100, includes an interface assembly 102, which has a top, antenna-engaging surface 104 and a bottom, tissue-engaging surface 106. The tissue-engaging surface is conformable, allowing it to conform to the tissue 108 over the area which is being treated. The top and bottom surfaces are visually transparent, allowing a visual view of the tissue through the interfacing assembly. Although the interfacing assembly is shown here as having a disk shape, other shapes can be used for the interfacing assembly. The interfacing assembly has a high relative dielectric constant, for example, dielectric constant $\in_r > 2$ (where $\in_r$ of vacuum is $\in_0 = 1.0$). The use of a high dielectric constant in the interfacing assembly helps the electromagnetic energy to efficiently couple into the tissue as discussed further below.

Disposed in a plane substantially parallel and adjacent to the top surface 104 is a balanced, circularly-polarized antenna 110. For example, as shown here, the antenna can be a twin-spiral antenna affixed to the upper (exposed) portion 112 of the top surface 104. Alternately, the antenna can be affixed to the lower (interior) portion 114 of the top surface, as discussed further below. The antenna includes sufficient open area to enable visual viewing of the tissue 108 through the antenna, as discussed further below.

Coupled to the antenna is a feed 116 to enable injection of electromagnetic energy into the antenna. For example, a cable as shown here can be used to conduct electromagnetic energy to the antenna from a signal generator or similar source. Alternately, the feed can be a connector to which a cable can be removably attached, for example, a SMA, BNC, or similar connector. Because the antenna is balanced, and a coaxial cable is unbalanced, a balun can be included to help reduce radiation from the feedline. Various arrangements of baluns can be applied in the context of the present invention as will occur to one of skill in the art, including for example wrapping the feed cable around a ferrite toroid.

Operation of the applicator 100 will now be explained. Electromagnetic energy is coupled through the feed 116 into the antenna 110, which causes the electromagnetic energy to propagate out from the antenna, radiating into the tissue 108. The high-dielectric constant interfacing assembly 102 helps to direct the radiated electromagnetic energy down, towards the tissue, rather than into the free space above the antenna. This directional coupling is due to several factors. First, the high dielectric interfacing assembly provides a lower characteristic impedance than the air above the antenna. For example, deionized water, having a relative permittivity of 78, can be used as the high dielectric material, as discussed further below, providing a characteristic impedance of about 40 ohms per square. This load is in parallel with the impedance of air of about 377 ohm per square. Hence, the electromagnetic radiation is directed generally into the dielectric providing approximately ten times more power being radiated into the dielectric below the antenna than into the air above the antenna. Second, the wavelength of the propagated electromagnetic radiation when measured in the dielectric material is significantly shorter than the wavelength in air. For example, at 915 MHz, the wavelength in water is 3.7 cm, as compared to 33 cm in air, and about 22 cm in most plastic materials. By using a relatively short antenna, for example a 3 cm diameter antenna, the antenna is quite short relative to the wavelength of the electromagnetic radiation in the air, but comparable in size to the wavelength of the electromagnetic radiation into the high dielectric material. Accordingly, radiation into the air is inefficient as compared to radiation into the high dielectric. In general, antenna diameters between 0.4 and 1.5 wavelengths (measured in the dielectric material) have proven desirable. Accordingly, the antenna can be dimensioned to be within this range for an intended operating frequency or range of operating frequencies for the electromagnetic energy. Other dielectric materials can be used, although it will be appreciated that low loss materials are desirable. Lossy materials can heat up, reducing efficiency of the applicator and displacing heating from the desired treatment areas. Coupling from the dielectric material into the tissue is efficient, because tissue also has a high dielectric constant, similar to that of water.

Figure 2:
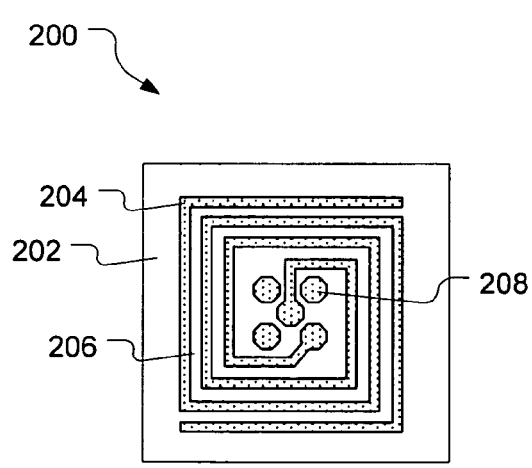
FIG. 2 is a top view of a square spiral antenna in accordance with an embodiment of the present invention.
Figure 3:
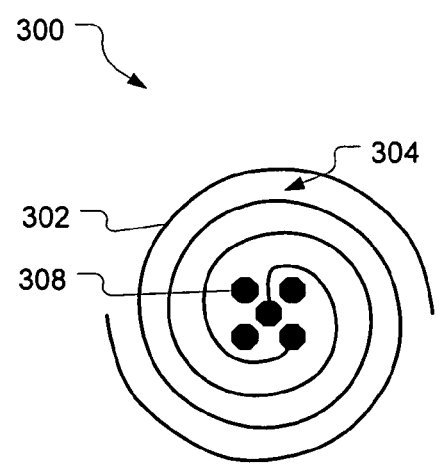
FIG. 3 is a top view of a circular spiral antenna in accordance with an embodiment of the present invention.

The directional coupling of power into the dielectric helps to avoid the need to provide shielding above the antenna. Accordingly, the antenna need not include a ground plane, which would ordinarily block viewing through the antenna. This allows the antenna to provide open areas through which the tissue can be viewed. The antenna is constructed as a balanced antenna, where two radiating elements are provided for opposite polarity connections to the feed. For example, the antenna can be a twin-spiral antenna, where one element is connected to one conductor of a feed (e.g., a center conductor of a coaxial feed), and the other element is connected to another conductor of the feed (e.g., an outer conductor of a coaxial feed). The antenna can be a square spiral, as shown in FIG. 2, a round spiral as shown in FIGS. 1 and 3, or various other configurations as will occur to one skilled in the art. The antenna 200, FIG. 2, can be formed on a transparent substrate 202, for example using printed circuit board techniques, to form the conductive elements 204. For example, elements of copper can be formed on a substrate such as Mylar or polystyrene. Open space 206 between the elements is thus transparent, allowing viewing through the antenna. For example, an antenna with a metal strip of about 1.7 mm width and strip separation distances of about 3 mm provides an impedance of about 30 ohms, and an open view area in excess of about 40%. Alternately, thin wire conductive elements 302, FIG. 3, can be used, allowing the antenna to provide a large open area 304 between the conductive elements 302. Open areas of at least greater than 50% can thus be accomplished. The antenna can include features to enhance connection to the feed, for example pads 208, FIG. 2, and 308, FIG. 3, for soldering a connector thereto.

Use of a circularly polarized antenna provides a circular polarization of the radiated electromagnetic field which helps to provide more uniform and symmetric heating of the tissue. Variations in the dielectric constant of the tissue (for example, between bone, muscle, fat, and tumor) cause significant variations when the electric field is perpendicular to an interface between tissues. For example, the interaction of electric fields with underlying tissues such as ribs along the chestwall varies quite a bit depending on the orientation of the electric field and the ribs. This is because, for example, at a frequency of 915 MHz the dielectric of the bone and fat of the body is about 5.6 and the other higher water content tissues such as muscle is about 54. Also, the conductivity of bone and fat is about 0.1 S/m where muscle tissue is 1.6 S/m. When the electric fields are oriented perpendicular to the ribs, there is a strong change of the electric field in the muscle between the bones as compared to the muscle overlying and underlying the bone where fields become more intense than between the bones. On the other hand, when the fields are aligned with the ribs the electric field is not greatly altered by the presence of the bone other than by some reflection by the bone that increase the fields overlying the bone and reduce the field below the bone.

The circular polarization of the electric fields tends to provide a stirring effect to smooth out these interactions.

An additional advantage of the circularly polarized antenna is improved broadband antenna characteristics. Reflections from the tissue tend to have reversed polarization relative to the antenna (e.g., a left-hand polarized antenna will emit left-hand polarized radiation, which, when reflected, will be right-hand polarized). The reduced coupling of reflections helps the antenna to present a more constant load as a function of operating frequency and tissue environment.

Because the interfacing assembly 102 and antenna 110 are visually transparent, this allows the tissue 108 to be visually monitored for adverse treatment effects while electromagnetic energy is being applied. For example, reddening of tissues commonly occurs prior to the formation of a heat blister or burn. Accordingly, a health care professional can visually monitor the skin for reddening, and take corrective steps prior to excessive heating. This is an improvement over prior applicators which were opaque, requiring the applicator to be removed in order to visually observe the treatment site. Accordingly, the applicator 100 can provide increased safety and effectiveness of treatment.

Continuing the discussion of FIG. 1, it will be appreciated that the side 118 of the interfacing assembly 102 can be, but need not be, transparent. The sides of the interfacing assembly can be semi-rigid, helping to provide a predefined spacing between the antenna 116 and the tissue-engaging surface 108, helping to enhance the uniformity of deposited electromagnetic energy into the tissue. For example, the interfacing assembly can be constructed from acrylic plastic (e.g. Plexiglass® acrylic sheet) to form a rigid antenna-engaging surface 104 and sides 108. A silicone rubber membrane can be affixed to the sides to form the flexible tissue-engaging surface 106 which has a dielectric constant of about 3. The interior can be filled with deionized water to provide a high dielectric constant as discussed above. The spacing between the antennas and tissue can be set to about 0.5 to 3.5 cm, although other spacing can be used as will be apparent to one of skill in the art. The antenna can be placed on the inside of the antenna-engaging surface, in direct contact with the deionized water. Placing the antenna close or in contact with the high-dielectric constant material helps to improve the efficiency, as discussed above. Optionally, the interfacing assembly can also include a mounting post (not shown) or similar feature to enable connection of the device to a support arm to help maintain the device in a desired position.

Figure 4A:
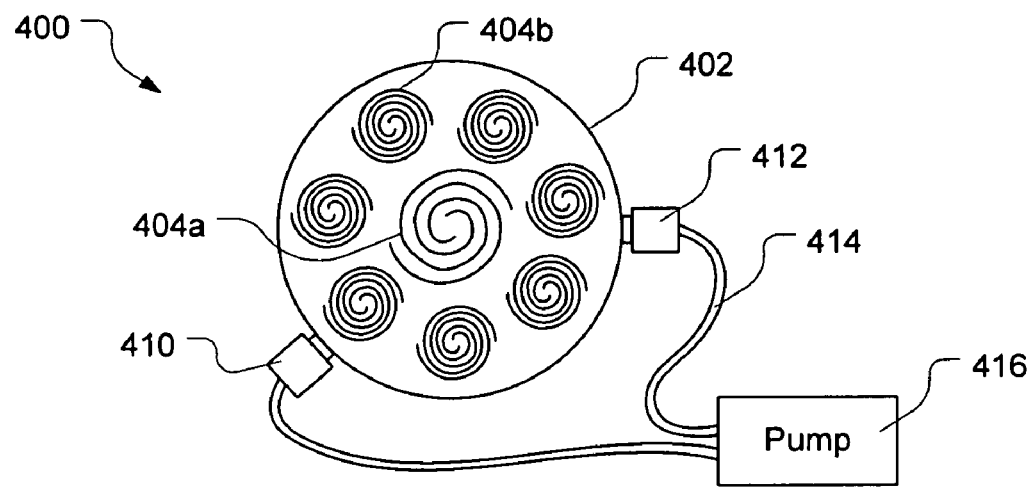
FIG. 4(a) is a top view of another applicator in accordance with an embodiment of the present invention.
Figure 4B:
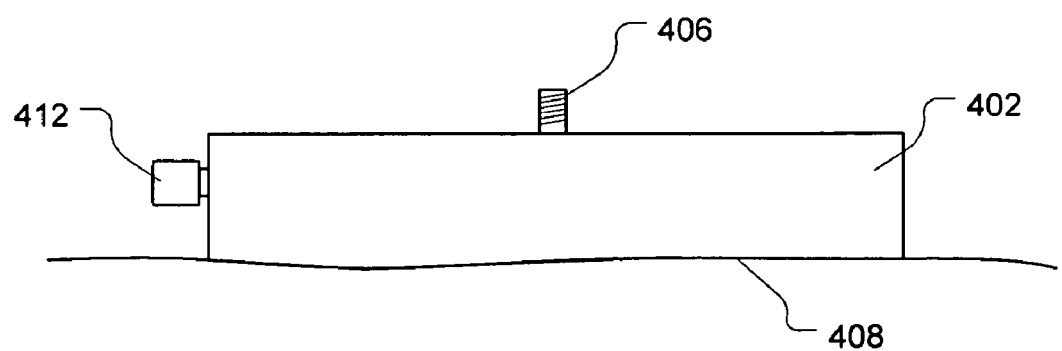
FIG. 4(b) is a side view of the applicator of FIG. 4(a)

An array of antennas can be used to provide a large treatment area as will now be described. FIGS. 4(a) and 4(b) illustrate an applicator for application of electromagnetic energy to an area of tissue in accordance with another embodiment of the present invention. The applicator, shown generally at 400, includes an interfacing assembly 402, to which is mounted an array of antennas 404. A single feed 406 is shown in FIG. 4(b). Alternately, a plurality of feeds can be included, and each feed coupled to one antenna or a group of several antennas. The interfacing assembly has a conformable bottom surface 408 as described above. The antennas are circularly-polarized balanced antennas as discussed above.

As can be seen, antennas within the array can have different configurations from each other. Here, eight spiral antennas are used, with the central antenna 404a having slightly larger dimensions than the outer ring of antennas 404b. This configuration may help provide a more even distribution of heating, although similar results may be obtained when the antennas are all approximately the same size.

Figure 5:
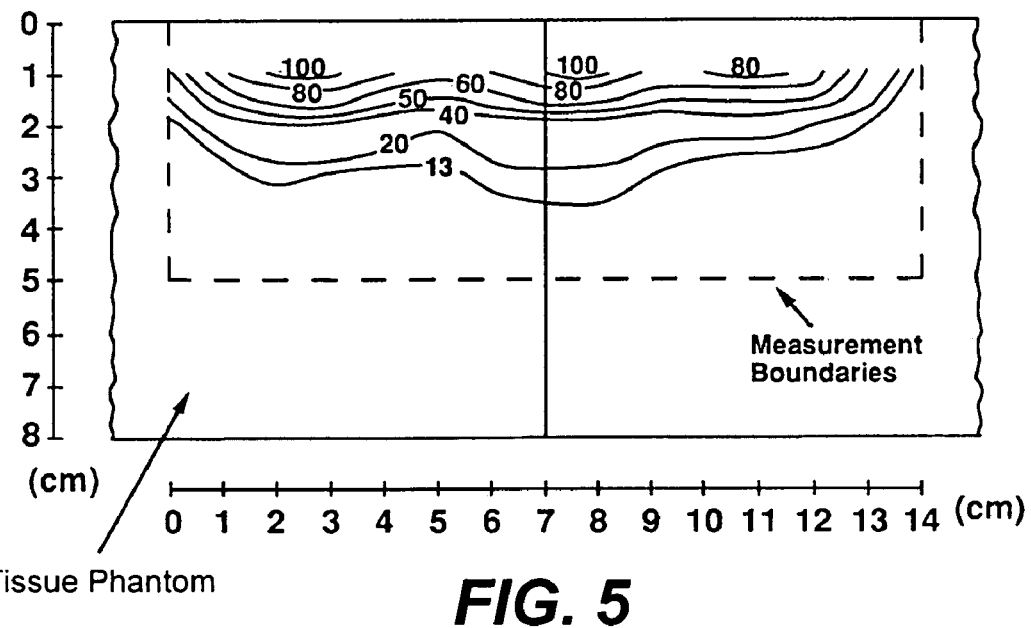
FIG. 5 is a side cross-sectional view of relative energy deposition profiles obtained in a phantom using the applicator of FIGS. 4(a) and 4(b)

FIG. 5 illustrates a side cross-sectional view of relative energy deposition profiles obtained in a phantom simulating human tissue when illuminated using the applicator of FIGS. 4(a) and 4(b). Various contours are shown, normalized to an energy deposition rate of 100 percent at a depth of 1 cm. Measurements were obtained using a tissue phantom equipped with a number of non-metallic temperature sensors. It can be seen that energy deposition in the tissue phantom is quite uniform. In contrast to linearly polarized arrays, less interaction occurs between circularly polarized arrays, helping to provide a more even heating distribution for superficial hyperthermia. Note that this is achieved without requiring a complex mechanical scanning arrangement.

The interfacing assembly 402, FIGS. 4(a) and 4(b), can be configured as a container in which a dielectric fluid, such as deionized water, can be disposed. The interfacing assembly can include a fluid inlet 410 and a fluid outlet 412. The inlet and outlet can be coupled, for example using tubing 414, to a pump 416 for circulating the dielectric fluid through the interfacing assembly. Circulating the dielectric fluid can help to maintain an even temperature at the surface of the tissue by removing air bubbles from the dielectric fluid and providing cooling or heating of the tissue surface. For example, cooling can help to avoid surface burning and/or to bias the heating profile toward deeper depths. The flow and cooling of the fluid can reduce bubble formation on the spirals that could modify the high dielectric loading of the antennas by the fluid medium.

Figure 6:
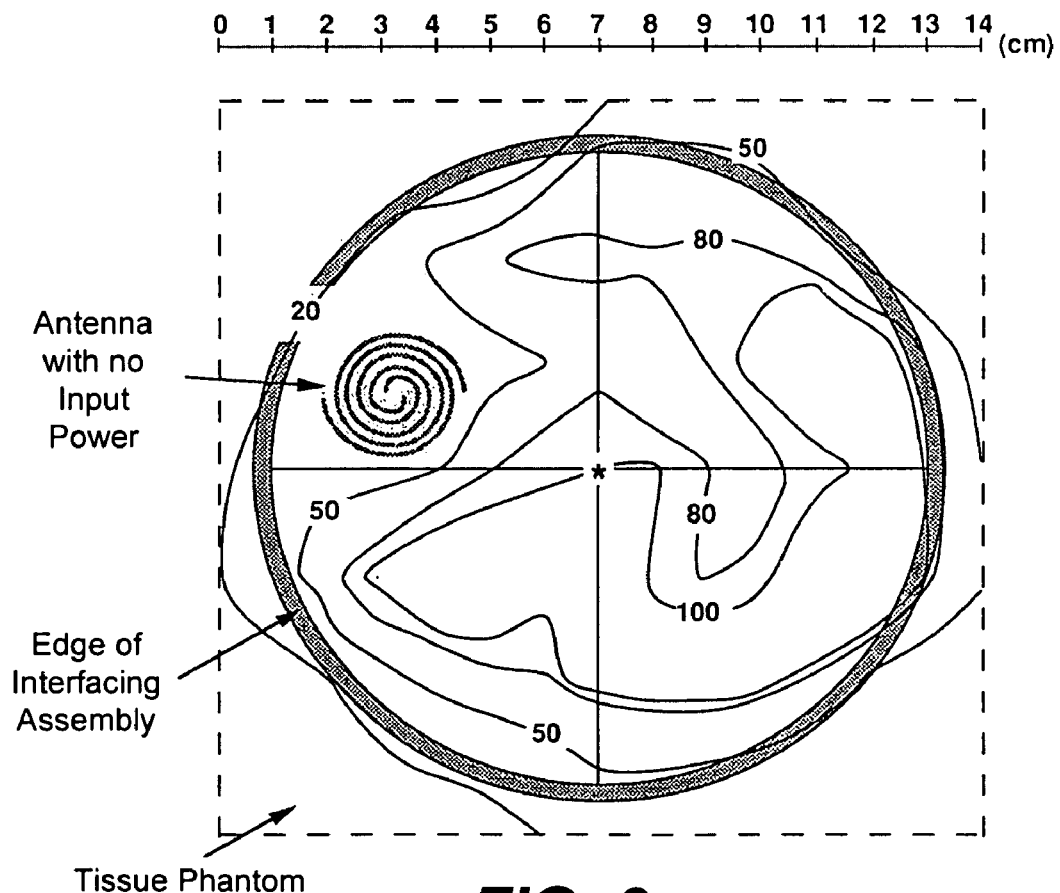
FIG. 6 is a transverse section of relative energy deposition profiles obtained in the phantom using the applicator of FIGS. 4(a) and 4(b) with no power applied to one antenna.

One benefit provided by an array of antennas with individually connected feeds is that the radiated power from the antennas can be adjusted as treatment progresses to change the pattern of energy deposition. Although the antennas can be operated with phase coherent electromagnetic energy applied, more uniform superficial heating may be achieved using incoherent energy. For example, FIG. 6 illustrates an energy deposition profile taken at a depth of 1 cm in a plane parallel to the tissue-engaging surface 408 of the applicator 400. Phase coherent power has been applied to all of the antennas 404 except one outer antenna 404b. It can be seen that the area under the antenna having no applied power is not heated substantially as compared with the other areas of tissue. This shows that the heating under the applicator with an array of antennas can be controlled by controlling the power radiated from individual antennas. A thicker dielectric fluid region can allow more interaction of coherent fields and result in less uniform heating.

Various ways of adjusting the power applied to the antennas will occur to one of skill in the art, including for example, a single source coupled to power splitters and attenuators, switch arrays, and multiple independent electromagnetic energy sources. For example, the BSD 500 system, available from BSD Medical Corp., Salt Lake City, Utah, provides eight independently phase, amplitude, and frequency controllable output channels which can be used to feed electromagnetic energy into respective individual antennas of an applicator. The BSD 500 can also provide phase incoherent operation between the microwave energy channels. Various feedback and control systems for directing control of the power can also be provided. For example, small temperature sensors, not shown, may be affixed to the tissue engaging surface of the applicator to monitor temperature of the tissue surface under each antenna group to serve as feedback to a power control system to control power applied to each antenna to generate a desired surface temperature. The power can also be controlled manually so that the power applied to individual antennas can be controlled, or automatic control can be overridden, in response to visually observed skin or tissue conditions.

Figure 7A:
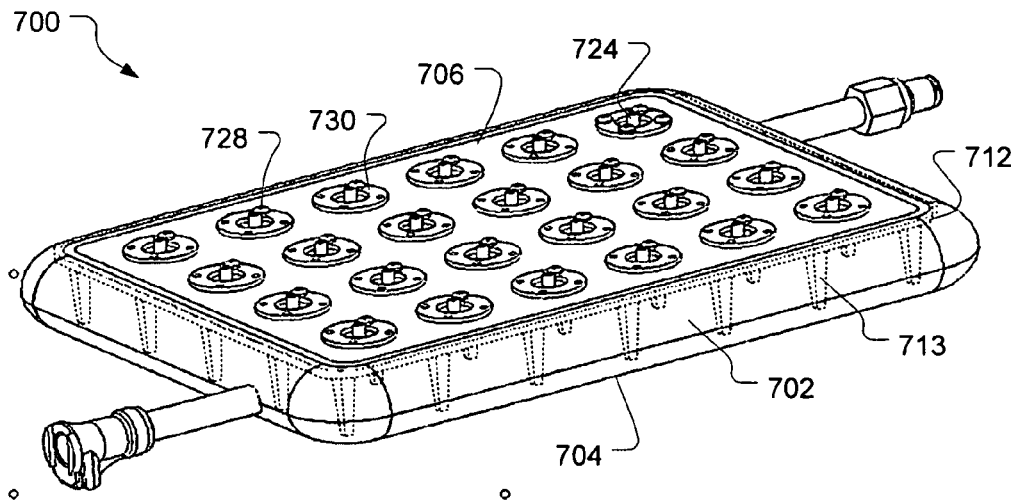
FIG. 7(a) is a perspective view of yet another applicator in accordance with an embodiment of the present invention.
Figure 7B:
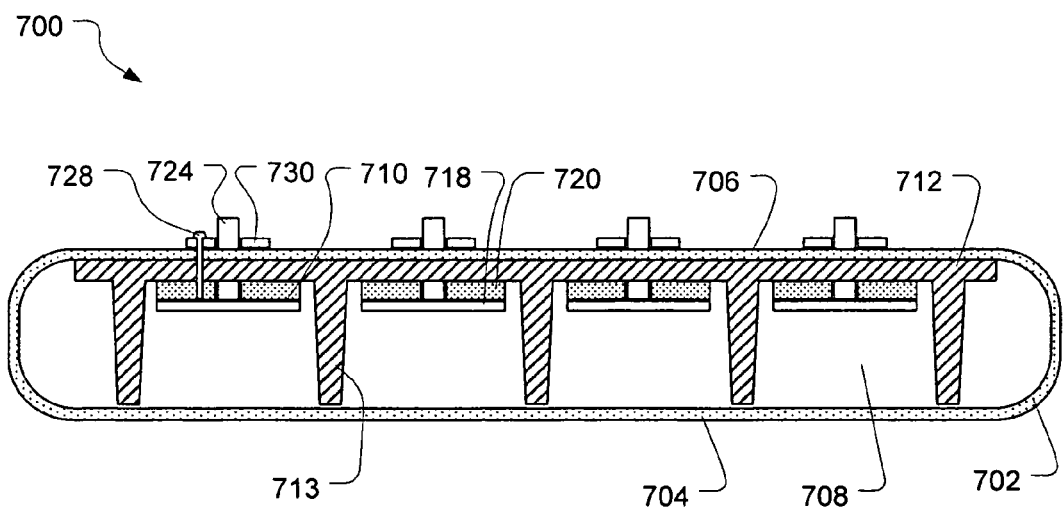
FIG. 7(b) is a side cross-sectional view of the applicator of FIG. 7(a)

An alternate applicator for application of electromagnetic energy to an area of tissue is illustrated in FIGS. 7(a) and 7(b) in accordance with yet another embodiment of the present invention. The applicator 700 includes a flexible, visually-transparent dielectric container 702, having a bottom tissue-engaging surface 704 and a top antenna-engaging surface 706. Disposed within the dielectric container is a transparent dielectric material 708, having a dielectric constant of at least 2.

An array of twin-spiral antennas 710 are disposed in a plane proximate to the antenna-engaging surface 706 of the dielectric container 702, mounted to a visually-transparent, flexible substrate 712. For example, the substrate can be a silicone rubber membrane. The substrate includes a plurality of protrusions 713 of predefined length extending toward the tissue-engaging surface. The protrusions help to keep the antennas at a predefined distance from the surface of the tissue. This in turns helps to maintain an even heating distribution.

The antennas 710 are substantially transparent. For example, the antennas can be formed from relatively thin wire and/or include substantial amounts of open area between the elements which can be viewed through as described above.

Figure 8A:
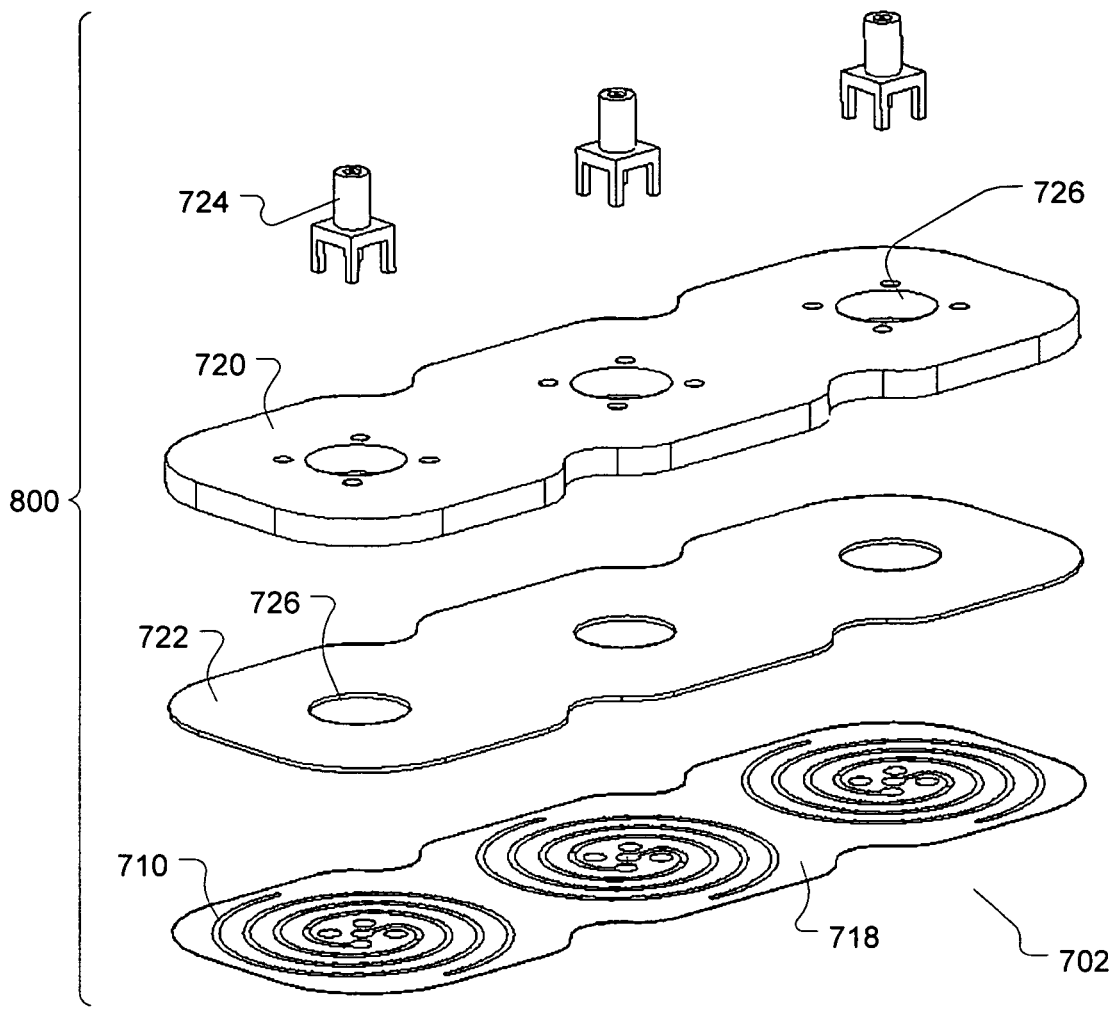
FIG. 8(a) is an exploded perspective view of an antenna group of the applicator of FIGS. 7(a) and 7(b)
Figure 8B:
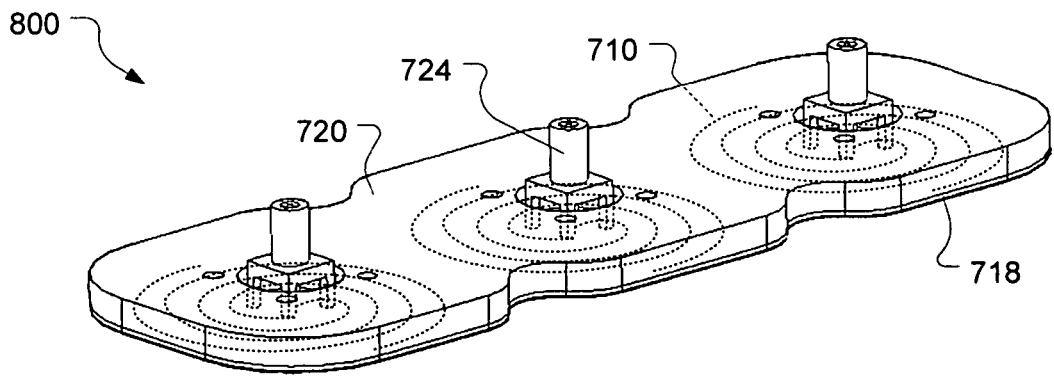
FIG. 8(b) is a perspective view of the assembled antenna group of FIG. 8(a)

The array of antennas 710 and substrate 712 are mounted inside the dielectric container 702. The antenna array is a rectangular array of four by six antennas, although other arrangements can be used as well. Groups of three antennas form an antenna group 800 as illustrated in FIGS. 8(a) and 8(b). The antenna groups are attached to the dielectric container 702 and membrane 712 to form the four by six rectangular array as shown in FIGS. 7(a) and 7(b). Two end-to-end sets of four side-by-side groups of three antennas will form the four by six array. The antennas in each group are sandwiched between a thin-dielectric membrane 718 on one side and a low-dielectric support 720 on the other side. The thin membrane 718 is thin enough so that the effective dielectric loading of the antenna is substantially the high dielectric fluid. The thin-dielectric membrane faces the tissue-engaging surface 706. For example, the low-dielectric support can be plexiglass or acrylic plastic, and the thin-dielectric membrane can be clear Mylar. Various ways of forming and fixing the antennas, membrane, and support together will occur to one of skill in the art, including for example using a glue layer 722. Feeds 724 extend through holes 726 in the support 720 and glue layer 722 and electrically connect to the antennas 710, for example by soldering to antenna contact pads 714, using either solder or an equivalent conductive epoxy.

The antenna groups 800 are affixed to the dielectric container 702 by screws 728 which screw from the exterior of the dielectric container, through holes in the top antenna-engaging surface 706 and membrane 712, into the support 720. The feeds 724 extend through corresponding holes in membrane 712 and in the top antenna-engaging surface 706 of dielectric container 702. Optionally, a compression ring 730 can be included to help the membrane form a seal with the dielectric container to help avoid dielectric fluid leaking from the dielectric container. The compression rings may be small and opaque or clear material. As another option, a separate seal or other sealing means can be used, as will occur to one skilled in the art.

Figure 9:
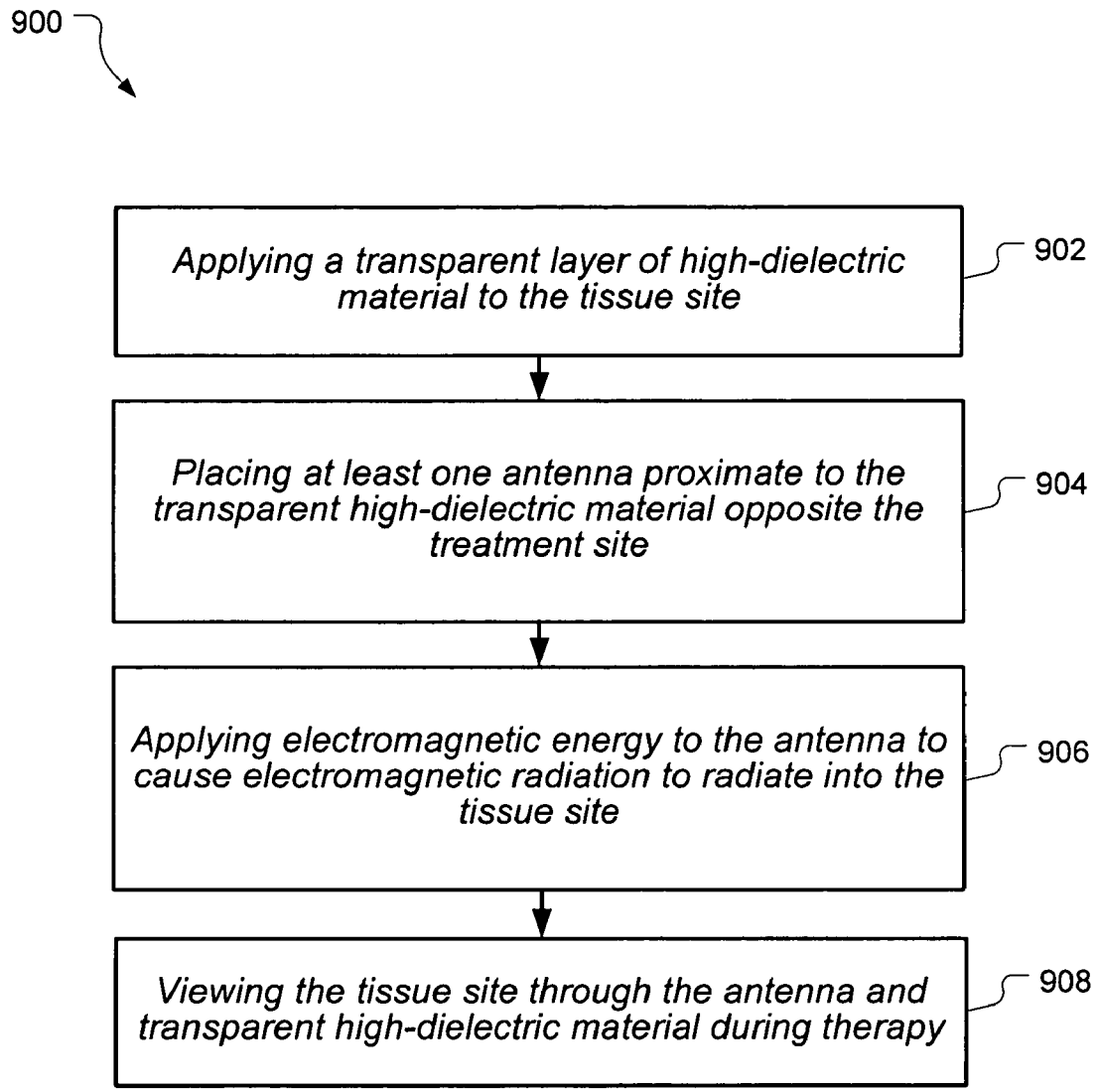
FIG. 9 is a flow chart of a method of performing hyperthermia therapy at a tissue site.

Finally, a method of performing electromagnetic heat therapy at a tissue site will now be described as illustrated in FIG. 9. The method includes the step of applying 902 a transparent layer of high-dielectric material to the tissue site. For example, a transparent interfacing assembly or transparent flexible dielectric container as described above can be used. Another step of the method is placing 904 at least one antenna proximate to the transparent high-dielectric material opposite the tissue site. For example, a single antenna or an antenna array can be used. The antenna(s) can be placed on top of or inside a container filled with high-dielectric fluid. Small temperature sensors may also be affixed to the membrane 704 to monitor temperature of the tissue surface under each antenna group to serve as feedback to a power control system to control the desired surface temperature.

Active treatment involves the step of applying 906 electromagnetic energy to the antenna(s) to cause electromagnetic radiation to radiate into the tissue site or the tissue under each antenna where the temperature is monitored. Various ways of generating electromagnetic energy suitable for use in embodiments of the present invention will occur to one skilled in the art. The placement of a high dielectric region between the antenna(s) and the tissue site causes the majority of the electromagnetic radiation to radiate into the tissue site.

During treatment, the step of viewing 908 the tissue site through the antenna and transparent high-dielectric material can be performed. Note that, because the high dielectric layer and antenna are transparent, viewing can be performed during active treatment, while electromagnetic radiation is being radiated into the tissue site. Accordingly, the tissue site can be monitored for indications of adverse treatment effects. Optionally, if contraindications are present, therapy may be ended, or the applied electromagnetic energy may be adjusted based on the appearance of the tissue site. For example, power levels applied to an array of antennas may be adjusted to change individual antenna power radiation levels as discussed above. Optionally, dielectric fluid can be circulated through a dielectric container holding the high-dielectric material during treatment, for example using a pump, as described above.

Summarizing and reiterating to some extent, an applicator for performing electromagnetic heat therapy in accordance with the present invention can help to avoid overheating or underheating in heat treatment therapy. The applicator provides non-invasive application of electromagnetic energy to an area of tissue. The tissue-engaging surface can automatically conform to the non-smooth contours typical of many diseased tissues, such as cancerous tissues, helping to maintain consistent spacing of the antenna or antenna array from the tissue. Optional protrusions or spacers within the dielectric can help to maintain even spacing. The consistent spacing in turn helps to promote more uniform transfer of EM energy into the tissue. Uniformity is also enhanced through the use of circularly-polarized, rather than linearly-polarized antennas.

Twin-spiral antennas, or other balanced circularly-polarized antennas, eliminate the need for a ground plane when loaded with a high dielectric material. This in turn allows the antennas to be mounted to visually-transparent materials, providing the ability to view the treatment area through the applicator. Visually monitoring the treatment site can help to avoid burns and allow adjusting the radiated energy as therapy progresses to enhance uniformity of the heating. For example, power levels to individual antennas in an array can be adjusted to compensate for excess heating in certain regions, for example as caused by differential blood flow, different tissue properties, and the like. Optional circulation of dielectric fluid can also help to control and/or maintain even surface temperature.

The terms "visually transparent" or "transparent" as used in this application refer to any material through which a person can look to visually observe the skin or tissue under the applicator. Thus, the material does not have to be completely clear, but can have a color tint or can have filtering properties. For example, Kapton (polyimide), which is a common material used as a substrate for metalization for antenna arrays, has a yellow tint to it but still enables viewing of the skin or tissue through such material. In addition, as explained above, the material does not have to be transparent over its entire surface, but only over enough of its surface so that a person can visually observe enough of the skin or tissue under the applicator to be able to monitor the skin or tissue for adverse effects of treatment. Thus, as indicated, a visually transparent antenna will usually have opaque conducting material with sufficient open space or area between the opaque conducting material so that a person can visually see and monitor the appearance of the skin or tissue below the applicator through the open space or area.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

We claim:

1. An applicator for application of electromagnetic energy to an area of tissue, comprising:
    a visually-transparent interfacing assembly, having a conformable visually-transparent tissue-engaging surface and an opposed antenna-engaging surface, wherein the interfacing assembly has a high dielectric constant;
    at least one balanced, circularly-polarized antenna disposed in a plane substantially parallel and adjacent to the antenna-engaging surface of the interfacing assembly, the antenna having sufficient open area to enable visual viewing of a tissue site through the open area within the antenna and the visually-transparent interfacing assembly; and
    a feed coupled to the antenna to enable injection of electromagnetic energy into the antenna.

2. The applicator of claim 1, wherein the visually-transparent interfacing assembly comprises a visually-transparent enclosure configured to contain a dielectric fluid therein.

3. The applicator of claim 2, wherein the visually-transparent enclosure contains deionized water.

4. The applicator of claim 2, wherein the visually-transparent enclosure further comprises a fluid inlet and a fluid outlet.

5. The applicator of claim 4, further comprising a means for circulating a dielectric fluid through the visually-transparent enclosure.

6. The applicator of claim 2, wherein the balanced, circularly-polarized antenna is disposed inside the visually-transparent enclosure.

7. The applicator of claim 1, wherein the visually-transparent interfacing assembly has a dielectric constant greater than 2.

8. The applicator of claim 1, wherein the balanced, circularly-polarized antenna is a twin-spiral antenna.

9. The applicator of claim 8, wherein the twin-spiral antenna is circular.

10. The applicator of claim 1, wherein the balanced, circularly-polarized antenna has at least a 40% open view area.

11. The applicator of claim 1, further comprising an array of balanced, circularly-polarized antennas disposed in the plane, the array having sufficient open area to enable visual viewing of the tissue-engaging surface through the array and the visually-transparent interface assembly.

12. The applicator of claim 11, further comprising a plurality of feeds, each feed coupled to a separate one of the balanced, circularly-polarized antennas in the array.

13. The applicator of claim 11, further comprising a plurality of feeds, each feed coupled to a group of the balanced, circularly-polarized antennas in the array.

14. The applicator of claim 1, wherein the balanced, circularly-polarized antenna comprises wire elements.

15. The applicator of claim 1, wherein the feed is a coaxial connector.

16. The applicator of claim 1, wherein the feed is a coaxial cable.

17. An applicator for application of electromagnetic energy to an area of tissue, comprising:
    a flexible, visually-transparent dielectric container having a bottom tissue-engaging surface and a top antenna-engaging surface;
    a visually-transparent dielectric material disposed within the dielectric container and having a dielectric constant of at least 2;
    an array of twin-spiral antennas disposed in a plane proximate to the antenna-engaging surface, wherein non-conducting area within and between elements of the twin-spiral antennas is transparent; and
    at least one feed coupled to the array of twin-spiral antennas and configured to conduct electromagnetic energy injected into the feed to at least one of the twin-spiral antennas.

18. The applicator of claim 17, wherein each twin-spiral antenna has a diameter between 0.4 and 1.5 lambda, wherein lambda is the wavelength of propagated electromagnetic energy in the dielectric material when the electromagnetic energy is applied to the at least one feed at an intended operating frequency.

19. The applicator of claim 17, wherein the array of twin-spiral antennas is sandwiched between a thin-dielectric membrane on one side and a low-dielectric support on the other side, with the thin-dielectric membrane facing the tissue-engaging surface of the dielectric container.

20. The applicator of claim 17, further comprising a visually-transparent, flexible substrate wherein the array of twin-spiral antennas is disposed on the visually-transparent, flexible substrate.

21. The applicator of claim 20, wherein the substrate is a silicone rubber membrane.

22. The applicator of claim 20, wherein the substrate further comprises a plurality of protrusions of predefined length extending toward the tissue-engaging surface.

23. The applicator of claim 17, further comprising a plurality of feeds, wherein each feed is coupled to at least one of the twin-spiral antennas.

24. The applicator of claim 17, further comprising at least one means for sealing a hole in the dielectric container, wherein the array of twin-spiral antennas is inside the dielectric container and the at least one feed coupled to the array of twin-spiral antennas extends through at least one hole in the antenna engaging surface of the dielectric container.

25. A method of performing hyperthermia therapy at a tissue site comprising the steps of:
    (a) applying a transparent layer of high-dielectric material to the tissue site;
    (b) placing at least one balanced, circularly-polarized antenna having sufficient open area to enable visual viewing of the tissue site proximate to the transparent high-dielectric material opposite the treatment site;
    (c) applying electromagnetic energy to the antenna to cause electromagnetic radiation to radiate into the tissue site; and (d) viewing the tissue site through the open area of the antenna and transparent high-dielectric material during therapy.

26. The method of claim 25, wherein step (a) comprises positioning a container filled with a high-dielectric fluid on the treatment site.

27. The method of claim 26, further comprising the step of (e) circulating the high-dielectric fluid through the container during treatment.

28. The method of claim 25, wherein step (c) comprises causing the majority of the electromagnetic radiation to radiate into the tissue site.

29. The method of claim 25, wherein steps (c) and (d) are performed simultaneously.

30. The method of claim 25, wherein step (d) comprises monitoring a visual appearance of the tissue site for indications of adverse treatment effects.

31. The method of claim 30, further comprising the step of (f) adjusting the applied electromagnetic energy based on the appearance of the tissue site.

32. The method of claim 25, wherein:
step (b) comprises placing a plurality of antennas proximate to the high-dielectric material opposite the tissue site; and
step (c) comprises applying electromagnetic energy to the plurality of antennas to cause electromagnetic radiation to radiate into the tissue site.

33. The method of claim 32, further comprising differentially adjusting the electromagnetic energy applied to the plurality of antennas based on an appearance of the tissue site.

34. The method of claim 25, wherein step (c) comprises heating a superficial area of tissue.

* * * * *